(12) United States Patent
Makino

(10) Patent No.: US 8,377,483 B2
(45) Date of Patent: Feb. 19, 2013

(54) BIOLOGICALLY ACTIVE AGENTS AND DRUGS

(75) Inventor: Shinji Makino, Aichi (JP)

(73) Assignee: I.B.E. Co., Ltd., Aichi (JP)

( * ) Notice: Subject to any disclaimer, the term of this patent is extended or adjusted under 35 U.S.C. 154(b) by 97 days.

(21) Appl. No.: 10/297,318

(22) PCT Filed: Jun. 5, 2001

(86) PCT No.: PCT/JP01/04753
§ 371 (c)(1),
(2), (4) Date: Dec. 4, 2002

(87) PCT Pub. No.: WO01/93879
PCT Pub. Date: Dec. 13, 2001

(65) Prior Publication Data
US 2003/0170315 A1    Sep. 11, 2003

(30) Foreign Application Priority Data

Jun. 6, 2000  (JP) .................................. 2000-168702
Jun. 1, 2001  (JP) .................................. 2001-165956

(51) Int. Cl.
*A61K 33/26* (2006.01)
(52) U.S. Cl. ......................................................... 424/648
(58) Field of Classification Search ........................ None
See application file for complete search history.

(56) References Cited

U.S. PATENT DOCUMENTS 4,950,486 A * 8/1990 Ayer et al. ...................... 424/473
5,008,097 A * 4/1991 Yamashita ...................... 423/493
6,495,177 B1 * 12/2002 deVries et al. .................. 426/72

FOREIGN PATENT DOCUMENTS

JP           02056409      *  2/1990

* cited by examiner

*Primary Examiner* — Alton Pryor
(74) *Attorney, Agent, or Firm* — Cooper & Dunham LLP

(57) ABSTRACT

The object of the present invention is to stabilize bioactivation of iron salt. Said object is attained by adding a magnesium salt to said iron salt. Said iron salt stabilized by said magnesium salt is useful as medicine to treat incurable diseases such as diabetes and growth promoting agent of animals and plants.

2 Claims, No Drawings

BIOLOGICALLY ACTIVE AGENTS AND DRUGS

FIELD OF INVENTION

The present invention relates to medicine and bioactivator useful as cosmetics, freshness preservative agent, growth promoting agent of animals and plants, and the like.

PROBLEM THAT THE PRESENT INVENTION INTENDS TO SOLVE

For instance, iron salt such as ferric ferrous iron salt is bioactivated and known to be useful as medicine, cosmetics, freshness preservative agent, growth promoting agent of animals and plants and the like.

Nevertheless, there is a problem that bioactive ability of said iron salt is unstable so that effect of said iron salt deteriorates during long preservation.

DISCLOSURE OF THE INVENTION

The gist of the present invention is that magnesium salt is added to said iron salt as stabilizer as means to solve the above described existing problem.

It is desirable that said iron salt and said magnesium salt are mixed together at a molar ratio in the range between 1:1 to $1:10^6$ and further, it is desirable that said bioactivator is prepared as aqueous solution and said iron salt in said aqueous solution is contained at a concentration in the range between $10^{-12}$ to 5 moles and further said iron salt is desirably ferric-ferrous iron salt. Further, the present invention provides treatment medicine of diabetes, hypertension, cancer, hepatitis, rheumatism, atopic dermatitis and the like said treatment medicine being said bioactivator.

DESCRIPTION OF THE INVENTION

The present invention is explained precisely hereafter.

Iron salt(s) of the present invention is(are) ferric-ferrous iron salt and/or ferrous iron salt and/or ferric iron salt.

[Ferrous Iron Salt, Ferric Iron Salt]

Ferrous iron salt and/or ferric iron salt, used as bioactivator in this invention, include inorganic acid salts such as hydrochloride, sulfate, nitrate, phosphate and the like, organic acid salts such as acetate, formate, oxalate, citrate, lactate, butyrate, succinate, propionate and the like, mixtures thereof. Two or more kinds of ferrous iron salt and/or ferric iron salt may be used together.

[Ferric-Ferrous Iron Salt]

Ferric-ferrous iron salt of the present invention is iron salt having properties between ferrous iron salt and ferric iron salt and said iron salt is such as inorganic acid salts (e.g. hydrochloride, sulfate, phosphate, nitrate and the like), organic acid salts (e.g. formate, acetate, oxalate citrate, lactate, butyrate, succinate, propionate and the like). Said ferric-ferrous iron salt is prepared by putting ferric iron salt in a large quantity of strong alkaline aqueous solution such as sodium hydroxide, potassium hydroxide, lithium hydroxide, calcium hydroxide and the like to cause valence conversion from ferric iron to ferrous iron or putting ferrous iron salt in a large quantity of strong acid aqueous solution such as hydrochloride acid, sulfuric acid and the like to cause valance convertion from ferrous iron to ferric iron and said ferric-ferrous iron salt is obtained as transition form during said valence conversion. Concrete illustrations of methods of production of said ferric-ferrous iron salt are shown hereafter.

Commonly, two methods described below are applied to prepare said ferric-ferrous iron salt.

1. Method 1 (Preparation from Ferric Iron Salt)

Ferric chloride ($FeCl_3.6H_2O$), 1.0 mg was dissolved in 100 ml of 0.5 N sodium hydroxide aqueous solution and stirred, then the solution was allowed to stand for overnight. After filtering out some insoluble products in the solution, the solution was neutralized with hydrochloric acid then concentrated in a reduced pressure desiccator to get a dried and crystallized product. Thus the crystallized product with sodium chloride, that is, chloride of ferric-ferrous iron (hereinafter sometimes referred to as iron chloride (II, III)), was prepared.

In case of extracting iron chloride (II, III) from the crystallized product with sodium chloride, the product was dissolved in 50 ml of 80% by weight isopropyl alcohol aqueous solution to elute iron chloride (II, III). After separating the solution containing eluted iron chloride (II, III), the solution was concentrated at reduced pressure in order to remove the solvent and dry. Then the procedure consisting of elution, concentration and dry was repeated a few times. Thus iron chloride (II, III), 0.25 mg was extracted from the crystallized product with sodium chloride.

2. Method 2 (Preparation from Ferrous Iron Salt)

Ferrous sulfate ($FeSO_4.7H_2O$), 1.0 mg was dissolved in 100 ml of 0.5 N HCl aqueous solution and stirred, then the solution was allowed to stand for overnight. After filtering out some insoluble products in the solution, the solution was concentrated in a reduced pressure desiccator to get a dried product. The dried product in powder was dissolved in 10 ml of 80% by weight isopropyl alcohol aqueous solution to elute iron chloride (II, III). After separating the solution containing eluted iron chloride (II, III), the solution was concentrated at reduced pressure in order to remove the solvent and dry. Then the procedure consisting of elution, concentration and dry was repeated a few times. Thus iron chloride (II, III), 0.6 mg was extracted from the crystallized product with sodium chloride.

Efficacy of bioactivation of said iron salts are as follows.

Ferric-ferrous iron salt>ferrous iron salt>ferric iron salt

[Magnesium Salt]

Magnesium salts, used in this invention, include inorganic acid salts such as magnesium chloride, magnesium sulfate, magnesium phosphate, magnesium nitrate, organic acid salts such as magnesium acetate, magnesium butyrate, magnesium formate, magnesium oxalate, magnesium citrate, magnesium propionate, and mixtures thereof. Two or more kinds of magnesium salts may be used together.

[Preparation]

Commonly said iron salt and said magnesium salt are respectively prepared as aqueous solution. In said aqueous solution said iron salt and said magnesium salt are mixed in a molar ration in the range between 1:1 to $1:10^6$ and commonly said iron salt is contained in said aqueous solution in a concentration in the range between $10^{-12}$ to 5 moles.

Further vitamin, hormone, fat and oil, perfumery spices, sweetening, and the like may be added in said aqueous solution.

Bioactivator of the present invention is mainly administered orally or by mixing in food as it is further said bioactivator can be administered by injection, instillation or percutaneously.

Said bioactivator of the present invention is especially useful for treatment or prevention of cancer, diabetes, hepatitis, nephritis, renal failure gastric ulcer, duodenal ulcer, hypertension, collagen disease, allergic diseases such as atopic dermatitis, pollinosis and the like, menorrhagia, obstipation, and the like and further useful as antimicrobial agent.

Further, said bioactivator of the present invention is useful as cosmetics since said bioactivator has beautificative action of skin besides preventive or treatment action of dermatitis and further said bioactivator has promotive action of growth of animals and plants and improving sense of taste.

[Action]

In the present invention, since iron salt useful as bioactivator is stabilized by magnesium salt, medicine, cosmetics, freshness preservative agent, growth promoting agent of animals and plants, and the like which can be preserved for longtime can be provided.

PREFERRED EMBODIMENT TO PUTTING THE INVENTION INTO PRACTICE

Example 1

Ferrous sulfate ($FeSO_4.6H_2O$), 1 g was dissolved in 5 ml of 12 N HCl aqueous solution and stirred. Then the solution was filtered by filter paper (No. 5C) to remove some insoluble products. A portion of the filtered solution for sampling was concentrated in a reduced pressure desiccator to get a dried product. The dried product in powder was dissolved in 80% by weight isopropyl alcohol aqueous solution. Then the solution containing eluted component was concentrated at reduced pressure in order to remove the solvent and dry. In addition, the procedure consisting of elution, concentration and dry was repeated a few times. Thus crystallized product was prepared.

5% by weight aqueous solution of the crystallized product, 0.01 ml was spotted on a point from 3 cm of the bottom of paper chromatography (PC) filter paper (2 cm×40 cm), then was developed by n-butyl alcohol:acetic acid:$H_2O$ (5:1:4, v/v/v) as developing solvent for 15 hours. After developing the filter paper was dried out then colored by spray of 1% by weight potassium ferricyanide aqueous solution as coloring reagent. As a result, it was confirmed that the developed point of the crystallized product was one spot (Rf=0.07).

In addition, a mixture of $FeCl_2$ and $FeCl_3$ was spotted on a paper chromatography (PC) filter paper as the same way. As a result, it was confirmed that there were two developed points ($FeCl_2$, Rf=0.095, $FeCl_3$, Rf=0.36) on the filter paper. These paper chromatography (PC) tests mentioned above accounted for the crystallized product as homogeneous product not mixtures.

Further, a sample solution, 100 ml was prepared by means of dissolving the crystallized product in distilled water. The sample solution (2.5 ml), 0.1% by weight orthophenanthroline aqueous solution (2.5 ml), and sodium acetate-acetic acid buffer solution, pH=4.5, (25 ml) were put into a mess-flask then distilled water was put into the mess-flask until its marked line. After being allowed to stand for 30 minutes at room temperature, an absorbance (510 nm) of the solution was measured. Ferrous iron in the sample solution was 0.019 g/100 ml calculated from standard curve, obtained by $FeCl_2$ solution in the same way.

Moreover, in the case of putting sample solution into the mess-flask, then hydroxyl mine hydrochloride aqueous solution, 1.0 ml was added to the mess-flask beforehand in order to reduce ferric iron in the sample solution to ferrous iron. As a result, ferrous iron, 0.038 g/100 ml was gotten. It was confirmed that the crystallized product consisted of ferrous iron and ferric iron equivalently because of calculation of ferric iron, 0.019 g/100 ml (=0.038 g/100 ml−0.019 g/100 ml). From consideration of the above-mentioned test, it was concluded that the crystallized product would be $Fe_2Cl_5.xH_2O$.

Example 2

Preparation of Ferrous-Ferric Iron Salt

Ferric chloride (1.0 mg) was dissolved in 5 ml of 10 N sodium hydroxide aqueous solution and stirred. After stirring, the solution was neutralized with 10 N hydrochloric acid, then was filtered by a filter paper (No. 5C) to remove some insoluble products. A portion of the filtered solution for sampling was concentrated in a reduced pressure desiccator to get a dried product. The dried product in powder was dissolved in 80% by weight isopropyl alcohol aqueous solution. Then the solution containing eluted component was concentrated at reduced pressure in order to remove the solvent and dry. In addition, the procedure consisting of elution, concentration and dry was repeated a few times. Thus the crystallized product was prepared. The crystallized product in this example was tested by the same way as Example 1 mentioned above. Thus, it was concluded that the crystallized product would be $Fe_2Cl_5.xH_2O$.

Example 3

Preparation of Bioactivator 1

Ferrous chloride ($FeCl_2$) anhydride and magnesium chloride ($MgCl_2$) anhydride were dissolved in water to prepare a bioactivator 1 in which $1\times10^{-1}$ mol/l ($FeCl_2$) and $2\times10^{-12}$ mol/l ($MgCl_2$) were contained.

Example 4

Preparation of Bioactivator 2

Ferrous sulfate ($FeSO_4$) anhydride and magnesium sulfate ($MgSO_4$) anhydride were dissolved in water to prepare a bioactivator 2 in which $1\times10^{-6}$ mol/l ($FeSO_4$) and $3\times10-6$ mol/l ($MgSO_4$) were contained.

Example 5

Preparation of Bioactivator 3

Ferric-ferrous iron prepared in Example 1 and magnesium chloride ($MgCl_2$) anhydride were dissolved in water to prepare a bioactivator 3 in which $1\times10^{-10}$ mol/l ($Fe_2Cl_5$) and $2\times10^{-8}$ mol/l ($MgCl_2$) were contained.

Example 6

Preparation of Bioactivator 4

Ferric-ferrous iron prepared in Example 2 and magnesium sulfated ($MgSO_4$) anhydride were dissolved in water to prepare a bioactivator 4 in which $1\times10^{-12}$ mol/l ($Fe_2Cl_5$) and $1\times10^{-2}$ mol/l ($MgSO_4$) were contained.

Example 7

Freshness Maintenance Test

Slices of a flatfish were dipped in the bioactivator 1 having been stored for 6 months after preparation, and then water was removed from said slices by a filter paper. Said slices wrapped in polyvinylidene chloride film were then kept at 5° C. K value (i.e. a value for determination of fish freshness) after said slices had been kept for 10 days was about 40 so that said slices of the flatfish were insufficiently eatable condition.

[Comparison 1]

Slices of the flatfish were dipped in an aqueous solution in which $1 \times 10^{-12}$ mol/l ($FeCl_2$) was contained and said aqueous solution had been stored for 6 months (without $MgCl_2$) in Comparison 1. After then, water was removed from said slices by the filter paper and said slices were then kept at 5° C. K value after said slices had been kept for 10 days was about 60 so that said slices at the flat fish was in barely eatable condition.

[Comparison 2]

The same maintenance test was carried out by using slices of the flatfish which was dipped in water as the test of Comparison 2. K value after said slices had been stored for 10 days was about 70 and said slices of the flatfish was in uneatable condition.

As the results of Example 7 and Comparison 1 and 2, it was recognized that $FeCl_2$ keeps sufficient effect to maintain freshness by adding $MgCl_2$ even after six months preservation.

Example 8

Using the bioactivator 2 which was prepared one year ago, pumpkins, potatoes and onions are cultivated. Conditions of said harvested vegetables were described below.

Pumpkins

Appearance: Having a glossy appearance and pulp is thick and has bright orange color and contains carotene as much as two times of ordinary pumpkins.

Taste: Being not soggy and tasting very good and sweet. Said pumpkin has a very high sugar content of 10.7 degree (generally 7 degree).

Potatoes

Appearance: Skin was white and having a little number of buds on the surface.

Starch: 18.6% (generally 16%).

Vitamin C: 32 mg/100 g (generally 23 mg/100 g).

Taste: Perfect degree of softness and being easily crushed in the mouth and having special smell and body of potato. Further, said potatoes are suitable for salad use since said potato has little harshness.

Onions

Appearance: Having a glossy appearance and uniform size. Skin can be easily peeled and pulp is tight and firm. Being storable for a long time. It was recognized by the electron microscope that said onion was a healthy crop having tissue in which small cells are packed closely.

Taste: Being easily cut by a kitchen knife and having good taste far eating raw. Since sugar content degree of said onion is very high, 10 degree, and has pleasant feeling on biting so that said onion is suitable for salad and does not crumble by frizzling.

Example 9

Medical Efficacy

In a case where said bioactivator 3 prepared in Example 5 is used as medicine, generally the following drinking method is applied.

(1) The following quantity of said bioactivator 3 is added in a cup of water (about 150 ml) and mixed well and said diluted bioactivator is drunk three times in a day, at getting up, before lunch, and before going to bed.

(2) Drinking quantity

First one week: 3 drops×3 times (9 drops in a day)

Second week: 5 drops×3 times (15 drops in a day)

Third week: 10 drops×3 times (30 drops in a day)

Forth week: 20 drops×3 times (60 drops in a day)

(3) Final drinking quantity a. Cancer: 30 drops×3 times (90 drops in a day)

b. Diabetes, Hepatitis, Gastric ulcer, Heart disease, Asthma, Hypertension, etc.: 20 drops×3 times (60 drops in a day)

c. Renal failure Rheumatism, Atopic dermatitis, Pollinosis, etc.: 10 drops×3 times (30 drops in a day)

d. Menorrhagia, Obstipasion, Sick from drinking, other slight diseases: 10 drops×one time (10 drops in a day)

e. Maintenance of health: 3 drops×3 drops (9 drops in a day)

The results in a case where said bioactivator 3 was administered to patients having various diseases according to above described drinking method are shown in Tables 1 to 14.

TABLE 1

| | | | | inspection data | | | | |
|---|---|---|---|---|---|---|---|---|
| cases | the name of a disease | patients sex | age | the blood sugar level *1 | HbA1c *2 | fat *3 | blood pressure *4 | observatin |
| 1 | diabetes | male | 69 | 318<br>281 | 9.2<br>10.2 | 331<br>235 | | Numerical value was improved as shown in Table after drinking for one week. |
| 2 | diabetes | female | 65 | 360<br>273 | | 172<br>126 | | Numerical value was improved as shown in Table after drinking for three months, and diabetic polyneuropathy was also improved at the same time. |
| 3 | diabetes | male | 58 | 328<br>119 | | | | Numerical value was improved as shown in Table after drinking for three months although dietetic treatment had been unstable. |
| 4 | diabetes | female | 58 | 316<br>141 | 9<br>6.2 | | | At the start to drink, taking 20 units of insulin and 2 tablets of blood sugar descending agent but stopped taking them and reduced blood pressure descending agent from 12 tablets to 4 tablets. |

TABLE 1-continued

| cases | the name of a disease | patients sex | age | inspection data blood sugar level *1 | HbA1c *2 | fat *3 | blood pressure *4 | observatin |
|---|---|---|---|---|---|---|---|---|
| 5 | diabetes | female | 60 | 287<br>87 | | | 143/76<br>123/74 | Inspection data was much improved and hypertension was also improved without dosage of blood pressure descending agent after drinking for three months. |
| 6 | diabetes | male | 55 | 131<br>80 | | | 142/88<br>126/88 | All subjective symptoms were much improved after drinking for three months. |
| 7 | diabetes | female | 39 | 336<br>190 | | | | She was a patient who was diagnosed by the other hospital that dosage of insulin was necessary, but numerical value was improved as shown in Table after drinking and taking only one tablet of blood sugar descending agent for three months in this hospital. |

Top: befor,

Bottom: after

*1 the blood sugar level: normal values 70–110 ml/dl

*2 HbA1c: normal values 4.0–6.0%

*3 fat: normal values 50–140 mg/dl

*4 blood pressure: normal values 139–101/89-61 mmHg

TABLE 2

| cases | the name of a disease | patients sex | age | inspection data the blood sugar level *1 | HbA1c *2 | fat *3 | blood pressure *4 | observation |
|---|---|---|---|---|---|---|---|---|
| 8 | diabetes | male | 55 | 458<br>98 | 12.4<br>5.4 | | | After leaving a general hospital, he was treated in this hospital. After drinking for one month, stopped dosage of insulin. Numerical value was improved as shown in Table after drinking for three months. |
| 9 | diabetes | female | 40 | | 12<br>7.6 | | | Injection of insulin by himself since he was 18 years old. He had had complete dietetic treatment and kinesitherapy and control of weigh so that there was no way excepting increasing dosage of insulin but numerical value was improved as shown in Table and dosage of insulin could be reduced. |
| 10 | diabetes | male | 40 | 823<br>89 | 13.8<br>6.2 | | | Numerical value was improved as shown in Table after drinking for three months. |
| 11 | diabetes | male | 65 | 247<br>93 | 8.7<br>6.8 | | | Stopped completely to take dosage of insulin after drinking for six months. |
| 12 | diabetes | female | 72 | 440<br>151 | 12.2<br>5.9 | | | He was a patient to whom a big quantity (32 units) of insulin had been given but dosage of insulin could be reduced to 22 units after drinking π water for three months and inspection data was improved. Further improvement is expected here after. |
| 13 | diabetes | female | 42 | 360<br>74 | 10.4<br>7.6 | | | He had insulin treatment for more than 20 years but improved on numerical value after drinking for three months even dosage of insulin was reduced. |
| 14 | diabetes | male | 59 | 316<br>140 | 8.5<br>5.9 | | | First taking 20 units of insulin and 14 tablets of oral medicine. |

TABLE 2-continued

|  |  |  |  | inspection data | | | | |
| --- | --- | --- | --- | --- | --- | --- | --- | --- |
| cases | the name of a disease | patients sex | age | the blood sugar level *1 | HbA1c *2 | fat *3 | blood pressure *4 | observation |
|  |  |  |  |  |  |  |  | After drinking for three months, dosage of insulin could be reduced to 0 and oral medicine could be reduced to 2 tablets. |

Top: befor,
Bottom: after
*1 the blood sugar level: normal values 70–110 ml/dl
*2 HbA1c: normal values 4.0–6.0%
*3 fat: normal values 50–140 mg/dl
*4 blood pressure: normal values 139-101/89-61 mmHg

TABLE 3

| cases | the name of a disease | patients sex | age | the blood sugar level *1 | HbA1c *2 | fat *3 | blood pressure *4 | fructosamine *5 | observation |
| --- | --- | --- | --- | --- | --- | --- | --- | --- | --- |
| 15 | diabetes | male | 55 | 520<br>85 | 12.4<br>55 |  |  |  | He had insulin treatment in the other hospital but there was no improvement before visiting this hospital. Completely recovered after drinking for less than one month. |
| 16 | diabetes | male | 53 | 311<br>96 | 12.3<br>7.4 |  |  |  | Improved by drinking for three months. He had high blood pressure and tookd the blood pressure descending agent but at present the blood pressure became normal and not necessary to take medicine. |
| 17 | diabetes | male | 48 | 668<br>87 |  |  |  |  | First he had taken insulin. After drinking for six months, he recovered to the condition that insulin taking was not necessary. |
| 18 | diabetes | female | 64 | 331<br>96 | 12.3<br>7.4 | 264<br>66 |  | 5.9<br>2.68 | After drinking for three months, diabetes was improved and fat value was also improved. |
| 19 | diabetes | female | 39 | 336<br>190 |  |  |  |  | She was in condition that medication of insulin was necessary but numerical value was improved without medication of insulin, as shown in Table after drinking for three months. |
| 20 | diabetes | female | 60 | 287<br>87 |  |  | 143/76<br>123/74 |  | She had complication of hypertension but much improved by drinking for one month without medication. |
| 21 | diabetes | male | 58 | 326<br>168 | 10.4<br>7.1 |  |  |  | Numerical value was improved as shown in Table by drinking for six weeks. |

Top: befor,
Bottom: after
*1 the blood sugar level: normal values 70–110 ml/dl
*2 HbA1c: normal values 4.0–6.0%
*3 fat: normal values 50–140 mg/dl
*4 blood pressure: normal values 139-101/89-61 mmHg

TABLE 4

| cases | the name of a disease | patients sex | age | inspection data blood pressure *1 | observation |
| --- | --- | --- | --- | --- | --- |
| 1 | high blood pressure | female | 51 | 182/100<br>146/68 | Numerical value became stable without oral medicine after drinking for one month. |
| 2 | high blood pressure and cerebrovascular infarction | female | 44 | 130/90<br>120/85 | Blood pressure had been barely kept in the range between 90 to 130 by taking three kinds of blood pressure descending agents (Ca-antagonist, |

TABLE 4-continued

| cases | the name of a disease | patients sex | age | inspection data blood pressure *1 | observation |
|---|---|---|---|---|---|
| 3 | high blood pressure | male | 60 | 178/106 139/84 | ACE inhibitor, β-blocker), but after drinking for three months, could stop taking these medicines. Subjective symptoms such as feeling of oppression in head, headache, lumbago, and the like were completely vanished after drinking for three months. |
| 4 | high blood pressure | male | 72 | 141/86 122/72 | Numerous value became stable by drinking for a week. |

Top: befor,
Bottom: after
*1 blood pressure: normal values 139-101/89-61 mmHg

TABLE 5

| cases | the name of a disease | patients sex | age | RBC *1 | WBC *2 | Hb *3 | Ht *4 | BUN *5 | CRP *6 | observation |
|---|---|---|---|---|---|---|---|---|---|---|
| 1 | systemic lupus erythematosus | female | 29 | 3.20 million 4.17 million | 9100 6300 | 7.2 11.8 | 22.8 36.2 | 29 16.9 | 4 0.1 | Normal numerical value was improved as show in Table after drinking for 12 months. |

Top: befor,
Bottom: after
*1 RBC = red blood corpuscles: normal values 3.5 million–4.5 million/mm$^3$
*2 WBC = white blood corpuscles: normal values 4000–9000/mm$^3$
*3 Hb = hemoglobin: normal values 2–15 g/dl
*4 Ht = hematocrit: normal values 36–45% (adult female)
*5 BUN = blood urea nitrogen: normal values 110 U/I (RIA; radioimmunoassay)
*6 CRP: normal values less than 1.0 mg/dl

TABLE 6

| cases | the name of a disease | patients sex | age | GOT *1 | GPT *2 | γ-GTP *3 | tumor marker AFP*4 | tumor marker TPA*5 | observation |
|---|---|---|---|---|---|---|---|---|---|
| 1 | cancer of the liver | male | 61 | 53 48 | 65 28 | 192.4 82.4 | | | Since he was diagnosed as liver cancer, he had been treated by taking anticancer drug. Confirmed by the checkup that numerical value had been improved as shown in Table after drinking three months. |
| 2 | cancer of the hepar | male | 57 | 126 57 | 73 39 | | 53.8 19.3 | 321 103 | Progressing viral hepatitis type C → Cirrhosis → liver cancer but the condition was improved and numerical valued tumor marker was also improved as shown in Table. |

Top: befor,
Bottom: after
*1 GOT: normal values 5–35 KU/ml
*2 GPT: normal values 5–25 KU/ml
*3 γ-GTP: normal values less than 40 units (adult)
*4 tumor marker AFP: normal values less than 20 ng/ml (RIA)
*5 tumor marker TPA: normal values less than 110 U/I (RIA)

TABLE 7

| cases | the name of disease | patients sex | age | tumor marker PAP *1 | tumor marker PSA *2 | CA125 *3 | CA19-9 *4 | observation |
|---|---|---|---|---|---|---|---|---|
| 1 | cancer of the prostate | male | 57 | 216 0.5 | | | | tNumerical value was improved as shown in Table by drinking for three months. |

TABLE 7-continued

| | | | | inspection data | | | | |
|---|---|---|---|---|---|---|---|---|
| cases | the name of disease | patients sex | age | tumor marker PAP *1 | tumor marker PSA *2 | CA125 *3 | CA19-9 *4 | observation |
| 2 | cancer of the prostate | male | 56 | | 3.8<br>0.8 | | | Completely recovered by drinking for two months. |
| 3 | ovarian cancer | female | 77 | | | 3000<br>7 | | Tumor having a size of about 5 cm had reduced to about 1 cm after drinking for six months, and numerical value was improved after one year as shown in Table. |
| 4 | cancer of the colon | male | 82 | | | | 42.3<br>32.1 | Numerical value was improved as shown in Table by drinking for two months. |

Top:befor,
Bottom: after
*1 tumor marker PAP: normal values less than 3.0 ng/ml (RIA)
*2 tumor marker PSA: normal values less than 3.0 ng/ml (RIA)
*3 CA125: normal values less than 50 U/ml
*4 CA19-9: normal values less than 37 U/ml

TABLE 8

| | | | | inspection data | | | | | | |
|---|---|---|---|---|---|---|---|---|---|---|
| cases | the name of a disease | patients sex | age | WBC *1 | white blood corpuscles *2 | blood platelets *3 | protein M *4 | CA 125 *5 | CA 19-9 *6 | observation |
| 1 | acute myelocytic leukemia | female | 45 | 1800<br>3700 | | | | | | Headache, stiff shoulders, nausea, dorsalgia, constipation, halitosis and the like wholly vanished, and physical condition was also improved after drinking for three months. |
| 2 | myelocytic leukemia | male | 59 | | 6000<br>9400 | 6100<br>177000 | | | | Numerical value was improved as shown in Table after drinking for 10 days. |
| 3 | multiple myeloma | female | 64 | | 2200<br>3600 | 30000<br>80000 | 10080<br>2120 | | | Numerical values of leukocyte and thrombocyte were improved to reach certainly to normal numerical values although present numerical values were still lower than normal numerical values after drinking for three months. |
| 4 | aplastic anemia | female | 34 | | | | | 2360<br>38 | 1060<br>87 | First, it was doubiful that this anemia was malignant by the inspection but numerical value was improved as shown in Table after drinking for three months, and it was confirmed that this anemia was benign. |

Top: befor,
Bottom: after
*1WBC: normal values 4000–9000/mm$^3$
*2 white blood corpuscles: normal values 4000–9000/mm$^3$
*3 blood platelets: normal values 0.2 million–0.4 million/mm$^3$
*4 protein M: normal values 1700/mm$^3$
*5 CA125: normal values less than 50 U/ml
*6 CA19-9: normal values less than 37 U/ml

TABLE 9

| | | | | inspection data | | | | | |
|---|---|---|---|---|---|---|---|---|---|
| cases | the name of a disease | patients sex | age | GOT *1 | GPT *2 | γ-GTP *3 | ZTT *4 | TTT *5 | observation |
| 1 | hepatitis | female | 53 | 73<br>34 | 97<br>33 | | | | There was no effect by medication of two kinds of herbal medicines but improved after drinking for one month. |

TABLE 9-continued

| cases | the name of a disease | patients sex | age | inspection data GOT *1 | GPT *2 | γ-GTP *3 | ZTT *4 | TTT *5 | observation |
|---|---|---|---|---|---|---|---|---|---|
| 2 | chronic viral hepatitis type B | male | 50 | 86<br>30 | 140<br>14 | | | | Numerical value was completely improved after drinking for three months. |
| 3 | viral hepatitis type B | male | 50 | 86<br>30 | 40<br>14 | | | | Numerical value was completely improved after drinking for one month. |
| 4 | viral hepatitis type C | female | 45 | 88<br>83 | 155<br>143 | 87<br>75 | 12.6<br>14 | | Function of liver began to be improved by drinking for one month. |
| 5 | viral hepatitis type C | male | 49 | 307<br>216 | 410<br>290 | 70<br>52 | 33.6<br>33.1 | 17.4<br>15.6 | Usually feeling overworked by hard work but improved by drinking for two months. |
| 6 | chronic viral hepatitis type C | female | 55 | 85<br>57 | 147<br>79 | 36<br>19 | 13.1<br>12 | 3.7<br>3.5 | Numerical value was improved as shown in Table. When drinking was stopped, condition changed for the worse. It has been improved and stable since she started to drink again. |
| 7 | chronic viral hepatitis type B | male | 65 | 85<br>14 | 210<br>8 | | | | Quantitative-qualitative analysis reaction of antigen of virus type C of hepatitis became minus by drinking for one year. |

Top: befor,
Bottom: after
*1 GOT: normal values 5–35 KU/ml
*2 GPT: normal values 5–25 KU/ml
*3 γ-GTP: normal values less than 40 units (adult)
*4 ZZT: normal values 2–14 units
*5 TTT: normal values 0–5 units

TABLE 10

| cases | the name of a disease | patients sex | age | inspection data GOT *1 | GPT *2 | γ-GTP *3 | ZTT *4 | TTT *5 | observation |
|---|---|---|---|---|---|---|---|---|---|
| 8 | viral hepatitis type C | female | 40 | 68<br>18 | 60<br>12 | | | | Normal numerical value was improved to normal value after drinking for two months. |
| 9 | chronic viral hepatitis type C | male | 51 | 88<br>48 | 122<br>69 | | | | Body condition and numerical value were improved as shown in Table after drinking for 12 months. |
| 10 | chronic hepatitis | male | 51 | 85<br>57 | 147<br>79 | | | | Numerical value was improved as shown in Table after drinking four months. |

Top: befor,
Bottom: after
*1 GOT: normal values 5–35 KU/ml
*2 GPT: normal values 5–25 KU/ml
*3 γ-GTP: normal values less than 40 units (adult)
*4 ZZT: normal values 2–14 units
*5 TTT: normal values 0–5 units

TABLE 11

| cases | the name of a disease | patients sex | age | inspection data CRP *1 | RF *2 | observation |
|---|---|---|---|---|---|---|
| 1 | multiple articular rheumatism | female | 63 | 1.6<br>0.7 | 109<br>94 | Numerical value was improved as shown in Table by drinking for one month. |
| 2 | rheumatism | female | 41 | 1.8<br>1.1 | | Numerical value was improved as shown in Table, and swelling and ache of fingers were also improved after drinking for two months. |

Top: befor,
Bottom: after
*1 CRP: normal values less than 1.0 mg/dl
*2 RF = rheumatoid factors: normal values less than 35 U/ml

TABLE 12

| | | patients | | inspection data | | | | | |
| --- | --- | --- | --- | --- | --- | --- | --- | --- | --- |
| | | | | Ige-RIST | cat | cedar | house dust | weeds | |
| cases | the name of a disease | sex | age | *1 | *2 | *3 | *4 | *5 | observation |
| 1 | atopic dermatitis | male | 39 | 4628 | 13.8 | 41.58 | ≧100 | 345 | Numerical value was improved as shown in Table, |
| | | | | 780 | 11.5 | 33.6 | 70 | 2.8 | and at the same time taking steroid medicine became not necessary. |
| 2 | atopic dermatitis | male | 39 | 476 | | | | | He had 37 years history of atopic but he can be |
| | | | | 332 | | | | | stopped taking seroid medicine by drinking for six months. |
| 3 | atopic dermatitis | male | 23 | 1671 | | | | | Condition was much improved and numerical value |
| | | | | 1270 | | | | | was also improved by drinking for five months. |

Top: befor,
Bottom: after
*1 Ige-RIST: normal values less than 280 IU/ml
*2 cat: normal values less than 0.34 UA/ml
*3 cedar: normal values less than 0.34 UA/ml
*4 house dust: normal values less than 0.34 UA/ml
*5 weeds: normal values less than 0.34 UA/ml

TABLE 13

| | | patients | | inspection data MRSA | |
| --- | --- | --- | --- | --- | --- |
| cases | the name of a disease | sex | age | *1 | observation |
| 1 | MRSA | female | 79 | positive | Methicillin-Resistant *Staphylococcus Aureus* (MRSA) positive |
| | | | | negative | changed to MRSA negative by drinking for three months. |

Top: befor,
Bottom: after
*1 MRSA: normal values negative

TABLE 14

| | | patients | | inspection data | | | | |
| --- | --- | --- | --- | --- | --- | --- | --- | --- |
| | | | | triglyceride | obesity index | γ-GTP | amount of urine | |
| cases | the name of a disease | sex | age | *1 | *2 | *3 | *4 | observation |
| 1 | obesity | female | 53 | 220 | +16.4% | | | Numerical value was improved as shown in |
| | | | | 172 | +8.9% | | | Table by drinking for two weeks. |
| 2 | emaciation and slight hepatopathy | female | 44 | | −18.6% −6.7% | 87 45 | | Numerical value was improved as shown in Table by drinking for six weeks. |
| 3 | chronic nenal | male | 42 | | | | 20–50 460 | Quantity of urine was reduced to numerical value as shown in Table after drinking for four weeks. |

Top: befor,
Bottom: after
*1 triglyceride: normal values 50–140 mg/dl
*2 obesity index: normal values −10–+10%
*3 γ-GTP: normal values less than 40 units
*4 amount of urine: normal values 500–2000 ml/day

Example 10

Cosmetics and Hair Restoring

Bioactivator 4 was applied on the hair of head of five persons for test, and number of fallen hair after washing hair was counted for each person. Average 7 fallen hairs were counted before treatment while average 2 fallen hairs were counted one month after application test.

Further, said bioactivator 4 was applied on the face, the back of the neck, and the hands of a person for test before playing golf on a fine day in May and no sunburn was recognized after playing golf. Further, said bioactivator was applied on her face everyday and as the result, spots and freckle reduced after one month.

EFFECT OF THE INVENTION

In the present invention the bioactive effect of iron salt is stabilized by magnesium salt and as the result, the bioactive effect of said iron salt does not degrade and constant stable effect is ensured. Especially the bioactivator of the present invention is useful for medicine to treat incurable disease such as diabetes growth promoting agent of animals and plants.

The invention claimed is:

1. A method for stabilizing bioactivation of ferrous iron salt comprising dissolving said ferrous iron salt in water to prepare a ferrous iron salt aqueous solution in which ferrous ion is generated by the ionization of said ferrous iron salt, dissolving a magnesium salt in water to prepare a magnesium salt aqueous solution in which magnesium ion is generated by the ionization of said magnesium salt, and mixing said ferrous iron salt aqueous solution and said magnesium salt aqueous solution together so that the adjusted molar ratio of said ferrous iron salt and said magnesium salt is in a range of between 1:1 and 1:3 wherein said ferrous ion is stabilized by said magnesium ion in the resulting aqueous solution mixture.

2. A medicine comprising ferrous iron salt stabilized by dissolving said ferrous iron salt in water to prepare a ferrous iron salt aqueous solution in which ferrous ion is generated by the ionization of said ferrous iron salt, dissolving a magnesium salt in water to prepare a magnesium salt aqueous solution in which magnesium ion is generated by the ionization of said magnesium salt, and mixing said ferrous iron salt aqueous solution and said magnesium salt aqueous solution, wherein said ferrous iron salt and said magnesium salt are mixed together at a molar ratio in the range between 1:1 to 1:3 molar ratio and said ferrous ion is stabilized by said magnesium ion in the resulting aqueous solution mixture.

* * * * *